US010165780B2

(12) United States Patent
DiTuro

(10) Patent No.: US 10,165,780 B2
(45) Date of Patent: *Jan. 1, 2019

(54) METHODS AND COMPOSITIONS FOR TREATING POLLUTION

(71) Applicant: Aqua Dynamic Solutions, LLC, Adamsville, RI (US)

(72) Inventor: John W. DiTuro, Pine Bush, NY (US)

(73) Assignee: Aqua Dynamic Solutions, LLC, Adamsville, RI (US)

( * ) Notice: Subject to any disclaimer, the term of this patent is extended or adjusted under 35 U.S.C. 154(b) by 252 days.

This patent is subject to a terminal disclaimer.

(21) Appl. No.: 14/313,909

(22) Filed: Jun. 24, 2014

(65) Prior Publication Data

US 2015/0057153 A1 Feb. 26, 2015

Related U.S. Application Data

(63) Continuation of application No. 12/300,734, filed as application No. PCT/US2007/069113 on May 17, 2007, now Pat. No. 8,790,725.

(60) Provisional application No. 60/800,953, filed on May 17, 2006.

(51) Int. Cl.
| | |
|---|---|
| *A61K 36/31* | (2006.01) |
| *A61K 36/00* | (2006.01) |
| *A61K 35/00* | (2006.01) |
| *C12N 11/12* | (2006.01) |
| *A01N 59/00* | (2006.01) |
| *C02F 1/52* | (2006.01) |
| *C02F 1/68* | (2006.01) |
| *C02F 1/72* | (2006.01) |
| *C02F 3/34* | (2006.01) |
| *A01N 25/00* | (2006.01) |
| *A01N 43/90* | (2006.01) |
| *A01N 65/26* | (2009.01) |
| *C02F 103/00* | (2006.01) |

(52) U.S. Cl.
CPC ............ *A01N 59/00* (2013.01); *A01N 25/00* (2013.01); *A01N 43/90* (2013.01); *A01N 65/26* (2013.01); *C02F 1/5263* (2013.01); *C02F 1/688* (2013.01); *C02F 1/72* (2013.01); *C02F 3/348* (2013.01); *C02F 1/722* (2013.01); *C02F 2103/001* (2013.01); *C02F 2103/005* (2013.01); *C02F 2103/007* (2013.01); *C02F 2303/02* (2013.01); *C02F 2307/00* (2013.01); *Y02W 10/37* (2015.05)

(58) Field of Classification Search
None
See application file for complete search history.

(56) References Cited

U.S. PATENT DOCUMENTS

| | | | |
|---|---|---|---|
| 3,242,055 A | 3/1966 | De Lucia | |
| 4,211,740 A | 7/1980 | Dean et al. | |
| 4,532,123 A | 7/1985 | Gardner | |
| 4,637,905 A | 1/1987 | Gardner | |
| 5,089,407 A | 2/1992 | Baker et al. | |
| 5,106,633 A | 4/1992 | Edens et al. | |
| 5,275,943 A * | 1/1994 | DiTuro | C02F 1/688 |
| | | | 210/601 |
| 5,302,102 A | 4/1994 | Haimer | |
| 8,790,725 B2 | 7/2014 | Dituro | |
| 2009/0111694 A1 | 4/2009 | Dituro | |

FOREIGN PATENT DOCUMENTS

| | | |
|---|---|---|
| EP | 0320483 | 4/1994 |
| WO | 2000007944 | 2/2000 |

OTHER PUBLICATIONS

Mumuni et al. (2013) European Scientific Journal vol. 9, No. 24: 214-229.*
Beltran-Heredia et al. (2009) J. Hazardous Materials 164: 713-719.
Borah et al. (2002) Cytologia 67: 235-243.
Dalen et al. (2009) Science World Journal vol. 4 (No. 4) 6-11.
Ghebremichael, et al. (2005) Water Research 39, 2338-2344.
Gidde et al. (2012) Inter. J. Engineering Res. Dev. vol. 2, Issue 1 pp. 14-21.
Lurling et al. (2010) J. Appl. Phycol. 22: 503-510.
Malusare et al. (2011) National Seminar Vision 2025, Technological Developments in Biological Sciences at Patkar-Verde College Mumbai.
Ndabigengesere et al. (1998) Environmental Toxicity vol. 19, pp. 789-800.
Niber et al. (1992) J. Applied Entomology vol. 113, Issue 1-5, pp. 202-208.
Silva et al. Water Treatment by coagulation with powdered seeds of Moringa oleifera in pouches.
Silva et al. (2012) Water treatment by coagulation with powdered seeds of Moringa oleifera in pouches. In Soil and Water Engineering. International Conference of Agricultural Engineering—CIGRAgEng 2012: agriculture and engineering for a healthier life, Valencia, Spain, Jul. 8-12, 2012, pp. P-0514 CIGR-EurAgEng, 2012.
PCT International Search Report based on PCT /US2007 /069113 dated May 21, 2008.
Office Action in U.S. Appl. No. 12/300,734 dated Jan. 19, 2012.
Office Action in U.S. Appl. No. 12/300,734 dated Sep. 27, 2012.
Office Action in U.S. Appl. No. 12/300,734 dated May 2, 2013.

* cited by examiner

*Primary Examiner* — Christopher R Tate
*Assistant Examiner* — Russell G Fiebig
(74) *Attorney, Agent, or Firm* — Greenberg Traurig, LLP; David J. Dykeman; Roman Fayerberg

(57) ABSTRACT

This invention relates to compositions and methods for improving water quality by enhancing natural bacterial processes and altering environmental conditions in situ. This is achieved by the manufacture and use of granules or tables composed of the inventive formulations.

5 Claims, 1 Drawing Sheet

METHODS AND COMPOSITIONS FOR TREATING POLLUTION

RELATED APPLICATIONS

This application is a continuation of U.S. patent application Ser. No. 12/300,734, filed Nov. 13, 2008, now U.S. Pat. No. 8,790,725, which is a national phase filing under 35 U.S.C. 371 of International Application No. PCT/US2007/069113, filed on May 17, 2007, and claims the benefit of and priority to U.S. Provisional Application No. 60/800,953, filed May 17, 2006, the entireties of these applications are hereby incorporated herein by reference for the teachings therein.

FIELD OF THE INVENTION

The present invention relates to novel methods and compositions for the treatment of water, wastewater and polluted surface waters. The invention enhances natural bacterial processes and alters environmental conditions in situ. This is achieved by the manufacture and use of granules or single layer pucks containing the invention formulations.

DESCRIPTION OF THE PRIOR ART

Pollution continues to be an enormous problem. Industrial, agricultural and residential effluents continue to pollute our waterways with organic, inorganic and metallic pollutants. Current treatments include removing polluted sediment, removing the pollutants, and then optionally returning the clean sediment to the environment. This method, however, is very disruptive and disturbing to the environment.

Another prior art technique employs time released preparations. Here, one or more ingredients would be released to alter the environment, followed by the germination of desired bacteria, which would break down the pollutants.

One example of this type of preparation is described in U.S. Pat. No. 5,275,943, which is incorporated herein by reference in its entirety. In this patent, a time release two layered tablet is employed. The first layer would dissolve and, for example, release oxygen. This oxygen would effervesce out of the top layer of the tablet, helping to correct anaerobia conditions and stirring up the sediment. Then, beneficial aerobic bacteria would be released to break down the pollutants.

This technique has several disadvantages. First, there is a time delay since the oxygen must effervesce, then the bacteria is released. Second, the formulation of a two layered tablet, sometimes called a table within a tablet, is expensive and time consuming.

OBJECTS OF THE INVENTION

It is an object of this invention to provide for methods and compositions for treating water pollution in potable water, ground water, wastewater and surface water.

It is a further object of this invention to treat water pollution in a rapid manner.

It is still a further object of this invention to treat water pollution with a preparation which there is no time-delay between the release of the ingredients which alter environmental conditions and the biological portion of the ingredients.

It is yet still a further object of the present invention to treat water pollution with a preparation which is not a tablet within a tablet or multi-layered. The solid compressed mixture of ingredients is homogenous and erodes in solution at a constant rate creating reactive plume.

It is yet still a further object of the present invention is the use of unique substrates for the microbes/yeasts/fungi, that have either neutral, positive or negative buoyancies in aqueous solution to acts as vectors to deliver the biological portion of the puck to particular area of the water to be treated without the necessity for mechanical mixing.

It is yet still a further object of the present invention is the use of naturally produced botanical fibers, extracts and proteins in place of commonly used toxic and synthetic compounds to aid in particle adherence and suspended solids flocculation. These fibers, extracts and proteins are incorporated in the compress matrix of the solid tablet or loose mixture of the granules.

These and other benefits of the instant invention are set forth below.

FIGURES

DETAILED DESCRIPTION OF THE INVENTION

Figure 1:
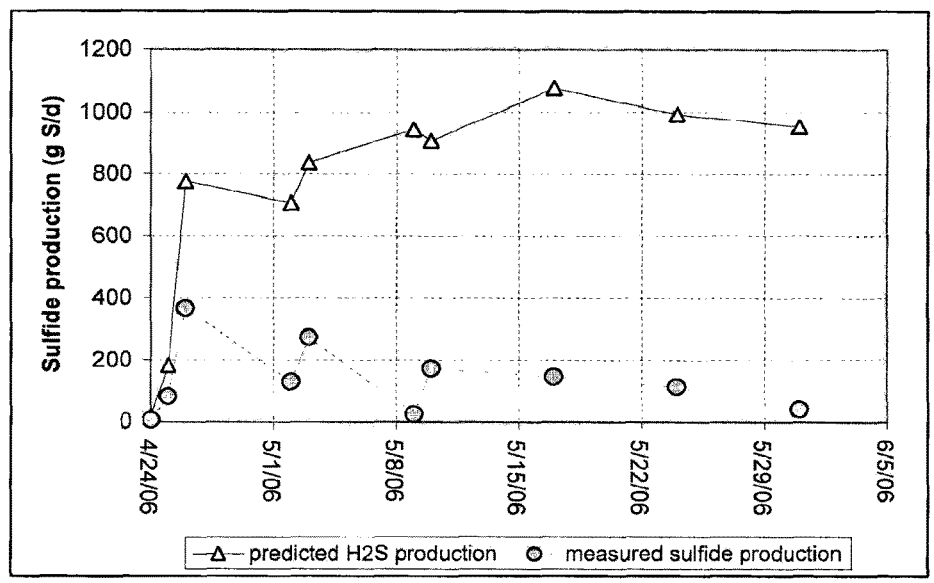
FIG. 1 is a comparison of measured liquid-phase sulfide production during Aqua-Puck Dosing period to predicted liquid-phase sulfide production using simple correlation equation based on TA-HRT and COD concentration.

Applicants have discovered that the instant preparations do not have to be time released because enough beneficial bacteria survive without time release to propagate and treat the pollution problem. Thus, for example, a tablet within a tablet formulation is not necessary. Likewise, to form granules, the ingredients can be simply mixed together. There is no need to formulate a tablet within a tablet and then grind that preparation up.

Also, the bacteria, used in the instant invention can be lyophilized to or incorporated in a substance which can sink, float or have a neutral buoyancy, thereby have control over where the bacteria will end up, the surface, suspended in the water column, or settle into the sediment. In addition, these substrates can exhibit a valance charge either anionic or cationic, thereby taking advantage of Van der Waal's attraction or electronegative repulsion to affect the net zeta potential of the effected solution.

In addition, the present invention uses a plant extract protein, and the protein exhibits a negative valence charge. This protein acts in solution by repelling similar charged particles and attracting oppositely charged particles. This movement, being caused by Van der Waal's attraction and electronegative repulsion, results in the alteration of the suspension's zeta potential. The protein attaches to pollutants with the opposite charge, increasing the suspended particles mass and precipitating them out of solution in a process called flocculation. The improved technique, outlined in this invention, replaces the commonly used method of using toxic Ferric or Aluminum Chloride or the newly developed synthetic polymers which are produced using toxic compounds, the procedure by which creates additional pollutants. Using the naturally occurring fibers, extracts and isolated proteins from plants and fungi such as drumstick tree (genus *Moringa*), Soapnut Tree (genus *Sapindus*), neem tree (genus *Azadirachta, Melia* or *Antelaea*), Caster tree seed (genus *Ricinus*) aloe vera (genus *Aloe*), prickly pair cactus (genus *Opuntia*) Guar Gum Tree (genus *Cyamopsis*), horseradish (genus *Armoracia* or *Cochlearia*), barley (genus *Hordeum*), Ryegrass (genus *Lolium*), Oats (genus *Avena*), Lucerne (genus *Medicago*), Yucca (genus *Yucca*), red clover (genus *Trifolium*), Mucoralean Fungi (genus *Actinomucor, Mucor, Cunninghamella* and *Syncephalastrum*) are less expensive, with better performance and are biodegradable and environmentally sustainable as a non-polluting natural resource.

Formulations for the purpose of improving water quality by enhancing natural bacterial processes and altering environmental conditions in situ are set forth below. This is achieved by the manufacture and use of granules or tablets composed of special formulations.

A. Surface Water Clarifier

This product addresses the problems of pond and lake pollution in the form of eutrophic conditions. These conditions are due either to over fertilization or lack of oxygen. These conditions result in the overgrowth of various forms of nuisance algae, leaving the water murky and the surface possibly covered with a filamentous algal mat. These nuisance forms of algae inhibit the growth of more beneficial species of aquatic plants. In addition, anaerobic conditions are generated due to the increased oxygen demand created by the decay of the dead plant and algal matter. The anaerobic bacterial degradation of decaying organic matter generates foul smelling odors and gases. Poor environmental conditions lead to fish kills as well as decreased viability of fauna and flora affecting the flood web (insects, amphibians, reptiles, birds, and plants).

This product provides an environmentally friendly alternative to the use of toxic metals and synthetic herbicides in the treatment and clarification of eutrophic surface waters. Preparation involves the blending of dry powdered botanical materials and chemical compounds and compressing them into larger granular or tabletized form in order to enhance their method of dispersion and speed the actives.

The purpose of this particular formulation is to clarify a body of water, such as a pond, lake, stream, lagoon or bay as well as inhibit the growth of a wide range of pest species of algae such as e.g., *Spirogyra, Cladophora, Pithophora, Lyngbia, Anabaena, Microcysitis* and *Cylindrospermopsis*, many of which do not respond well to commonly used herbicidal treatments such as copper sufate. A blended mixture of powdered botanical material (such as dehydrated barley straw, rye grass leaves, red clover leaves, lucerne leaves), oxidative alkali (such as sodium carbonate peroxyhydrate, sodium perborate, sodium peroxide) and a clarifying agent such as activated botanical proteins (such as those found in the plants in the genus *Morgina*) is used. An additional variant which contains oil of the neem tree, *Azadirachta indica*, for use in controlling mosquito infestation in standing surface waters, can also be added. The formulation may also include microorganisms that aid in the process of breaking down the barley straw particles and may also help to reduce the settled sludge (decaying organic matter and detritus) at the bottom of the pond or waterway. The type of microbes can include bacteria, such as the strains from the genus *Bacillus* (eg. *Bacillus licheniformis— Bacillus subtilis, Bacillus polymyxa, Bacillus megaterium*) *Pseudomonas* (eg. *Pseudomonas putida*) and *Lactbacillus* (e.g. *Lactobacillus* sp.).

B. Wastewater Treatment

The purpose of this product is to improve the quality of water by improved clarification (lowering of dissolved and suspended solids and biochemical oxygen demand), in situ reduction of hydrogen sulfide, ammonia and volatile fatty acid and the enhanced microbiological breakdown of fats, oils and greases.

There are a number of problems related to wastewater treatment. The wastewater is confined and in low flow conditions, which leads to anaerobic conditions. Anaerobes generate sulfides, ammonium ions, volatile fatty acids, and methane. Intermittent flows (due to changes in water demand during the day) exacerbates the anaerobic buildup of gases (H2S, NH3, and Volatile Fatty Acids) dissolved in solution causes the massive release of the odorous gases from solution (degassing, or purge) as a slow flow suddenly increases. Also, laminar flow results in no flow at the surface of the wastewater. These conditions can result in the escape of noxious gases, corrosion, bacterial slime and lack of oxygen.

The present invention treats these problems as follows:

1) Rate of Settling of Suspended Solids is Increased Due to:

Mechanical action of rising oxygen bubbles provided by the inventive granules or pucks forces particles closer together, increasing the change of agglomeration. The agglomerated particles have increased mass and there fore are able to overcome forces restricting their settlement (e.g. water flow, phase differences, thermoclynes).

The botanical flocculants that are released into the solution as the inventive puck or granules disintegrate act as a seed particle for the removal of dissolved solids from solution. An example is the removal of dissolved calcium in the form of carbonates from a concentrated solution. As the calcium adheres to the charged protein particles, they act as substrate base for the formation of crystal complexes which grow larger and more massive. As their mass increases, so also does their settling rate. Removing dissolved electrolytes from solution also affects the solutions zeta potential and enhances the process.

2) Prevention of Formation Odors and Noxious Gases that Lead to Acid Corrosion (Hydrogen Sulfide, Ammonia, Volatile Fatty Acids):

Achieved by purging dissolved gases out of solution by the physical action of bubbling a gas through the solution (Henry's Law).

By using oxygen as the gas for this purpose, aerobic conditions can be maintained, preventing the generation of gases and compounds that are created anaerobically. By preventing these gases, the present invention prevents their condensates (sulfuric and nitric acids) which cause infrastructure (pipes, tanks, enclosures, hardware etc.) damage.

Existing acids are neutralized by chemical reaction with alkaline buffers and the oxidation of dissolved organic acids.

Dissolved hydrogen sulfide is chemically bonded to form a precipitant salt, by interaction with unique activated form of a botanical extract (of a plant in the genus *Ricinus* or *Moringa*) that has preferably been sphereulated and coated to form a dry flowable powder.

3) Inoculate Water and Surface FOG (Fats, Oils, Greases), with Specific Microorganisms (Bacteria, Fungi And Yeasts).

These organisms can either be in a dry sporeulated form that has been lyophilized onto a substrate or in a suspended vegetative state which is then encapsulated into the structure of a micro-sponge.

The types of microbes can include bacteria from various species and strains from the genus *Bacillus* (e.g. *Bacillus licheniformis, Bacillus subtilis, Bacillus polymyxa, Bacillus megaterium*) and *Pseudomonas* (eg. *Pseudomonas putida*) and various species and strains of fungi (e.g. *Hanerochaete chrysosporium* and *Aspergillus niger*)

The buoyancy of the substrate material can be chosen specifically to ensure that the specific microbes are transported to their designated destination (surface, middle water column, or bottom sediment).

Micro-nutrients and environmental adjusters can be included to ensure proper germination of microbes.

Through the adjustment of nutrients, buffers, additives and correct species of microbes a special preparation can be made to treat greases (restaurant grease trap wastes) and convert it to yellow grease (clean oils of similar molecular weight) as a feed stock for the production of biodiesel, an alternative fuel source form crude petroleum based fuels (e.g. fuel oil, and natural gas).

A special device can be employed to aid in the processing of this gray grease which employs ultrasonic sound waves and or light waves.

Device for storing, then applying pucks to a wastewater stream, wastewater holding tank or grease trap.

4) Use in the Treatment of Portable Toilet Waste, Both in Holding Containers and in Transport.

This includes all the advantages and treatment processes described in the treatment of wastewater above.

Pucks also include a non-toxic and biodegradable dye to color the treated water (most commonly blue).

The dye or dyes chosen have to remain stable (color fast) in a highly acidic (due to urine) environment for the amount of time the waste remains in the toilet (3 to 7 days).

In addition the, puck will contain a non-toxic and biodegradable fragrance used to mask the waste odor, and make the atmosphere in the portable toilet more pleasant.

Also, the puck may contain additives that bind the odorous compounds such as hydrogen sulfide. (An example of which is a derivative of *Ricinus communis* seed extract.)

5) a Variation of Puck Formulation for Use in Removal of Arsenic and Chromium from Water (Groundwater, Surface Water, and Process Water).

Use of (lime) (0.1%) to coagulate and micro-filter.

Puck uses activated botanical proteins and acids (from the genus *Moringa* and *Aloe, Opuntia, Cyamopsis, Yucca, Actinomucor, Mucor, Cunninghamella* and *Syncephalastrum*) to coagulate and chemically bind metals.

Puck may contain activated botanical extracts of plants from the genus *Morgina* that has been processed into a dry flowable powdered form. This compound binds hydrogen sulfide (a compound that inhibits metals removal) and takes it out of solution.

May be used in conjunction with water filtration devises specifically designed to take advantage of the properties of said proteins.

Puck also contains and oxidative alkali such as sodium percarbonate, calcium peroxide.

In addition, puck may contain calcium oxide, ferric sulfate, activated alumina, bentonite clay and powdered zeolite, to aid in the process of metals removal.

C. Drain Treatment—Insect Control

This product is used as a drain clarifier and standing water treatment to reduce and eliminate flying pest infestation. The invention provides an environmentally friendly alternative to the use of toxic metals and chemical pesticides in the prevention of fruit fly and other nuisance and pest fly infestation. This is a granular mixture of the extract oil of the neem tree (*Azadirachta indica*) containing a high concentration of the active ingredient azadirachtin, sodium percarbonate and sodium carbonate, and may include fragrance, surfactant, microbes and enzymes.

Preparation involves the blending of dry powdered effervescent alkali with botanical materials and other chemical compounds as well as oil extract of the neem tree seed.

When the mixture is applied to floor drains, the alkali effervesces, distributing the oil throughout the standing water and incorporates it into the occlusion of oil and grease on the walls of the pipes.

When flies come in contact with oil extract which contains the limonoids, azadirachtin, salannin, and deacetylgedunin, compounds that inhibits fly instars development, they loose their fecundity, with larval mortality between the 1st and 3rd instar.

The infestation is eliminated once the adult flies perish in two to four weeks.

Formulations

Pond Treatment Puck

This product forms stable and structurally sound pucks (or tablets) with increased hardness and limited friability and lack of shearing using the listed ingredients in a 2.5" to 3" tablet diameter size with a weight of about 150 grams. When placed in solution the puck will disintegrate fairly quickly which is useful. Here, one sees the complete dispersion of the powdered ingredients throughout the water column leading to their rising to the water surface, rather than staying in a lump at the bottom.

Tablet Manufacture

In the past there were several production issues that were not overcome:

Pucks were made using both a stokes single station R press at 20 Klbs above and below with a 2.5" diameter and a 6" max. depth of fill and a Colton 16 station rotary with a 3" tablet diameter and 12" max depth of fill and 40 Klbs above and below. The tablets were made using a straight mixture of ingredients. Tablet size varied greatly due to variation in particle size, with the larger particles migrating to the tablet surface. Test samplings were made to get a handle on particle size distribution. This enabled us to narrow in on an acceptable size range in the 150 gram per puck range.

Shearing was found present in both types of tablets as well as particle size stratification and uneven tablet head surface. The shearing is thought to be the result of the inability to release the trapped air within the straw particles during the compression stroke. This problem can be overcome by making a tapered die to improve the air removal.

The incompressibility of the straw leads to pucks that would relax over time and would become less hard and very friable. This would lead to poor tablet stability with tablets coming apart in shipment due to friction with other tablets in bulk packaging. This problem can be overcome by grinding the ingredients into smaller size particles.

The sieve size (straw particle size screening) turned out to be a critical factor for success in tablet compression (too large and too small resulted in poor tableting results). The correct sieve size is to use in the present invention has been determined to be below a size six.

The bulk density of the tablets was reduced due to the high percentage of straw used in the formulation. This led to tablets that would float as the percarbonate would effervesce. So, rather than disintegrating, the tablet would stay intact, continually floating and sinking. This reduces the tablet's performance. It is better to have a dense tablet that sinks to the bottom and disintegrates with the ingredients being continually disbursed throughout the water column. This can be accomplished by using denser filler and binder materials.

Also, there was an issue with foaming, probably due to the stearate used to lubricate the press. It was added at about a 0.5 to 1.0% by weight and was insoluble. It was found that magnesium stearate or sodium stearate can be used.

Tablet Ingredients 1. (40-60%) may contain some or all of the following botanicals—dehydrated, pulverized, screened and powdered drumstick tree seed (genus *Moringa*), Soapnut Tree seed shell (genus *Sapindus*), neem tree seed oil (genus *Azadirachta, Melia* or *Antelaea*), Caster tree seed (genus *Ricinus*) aloe vera leaf (genus *Aloe*), prickly pair cactus leaf and fruit (genus *Opuntia*) Guar Gum Tree seed (genus *Cyamopsis*), horseradish root (genus *Armoracia* or *Cochlearia*), barley chaff (genus *Hordeum*), Ryegrass leaf (genus *Lolium*), Oat chaff (genus *Avena*), Lucerne leaf (genus *Medicago*) Yucca leaf (genus *Yucca*), red clover leaf (genus *Trifolium*), Mucoralean Fungi (genus *Actinomucor, Mucor, Cunninghamella* and *Syncephalastrum*).
2. (10-30%) AppTec Aqua Kleer® *Moringa oleifera* seed protein powder.
3. (20%) sodium carbonate peroxydrate—granular and coated, and stabilized.
4. sodium carbonate—(% varies to makeup difference in formulation weight) particle size similar to percarbonate, which is about size four.
5. (5-7%) binders and fillers—polyethylene glycol 6k, polyvinyl pyrrolidone (pvp) k-30, shellac natural gum, microcrystalline cellulose (mcc), lactose, hydroxypropyl methyl cellulose (hpmc), ethyl cellulose (ec), sodium chloride, talc.
6. (0-5%) W and W/O bacterial product (eg. *Bacillus licheniformis, Bacillus subtilis, Bacillus polymyxa, Bacillus megaterium, Pseudomonas putida*, and *Lactobacillus* sp.)

B. Grease Trap Mini Pucks

This product forms stable and structurally sound, odor reduction mini-pucks (or tablets) using the listed ingredients in a 0.75" to 1.5" tablet diameter size with a weight of about 50 grams per mini-puck. These tablets can be produced specifically for a client to enhance performance within the client's proprietary mechanical grease separating device, such as Big Dipper Grease Traps and the Greaseaway Automated Traps. This device automatically skims floating oil and grease off the surface and removes it into a separate container by having it stick to an electrostatically charged rotating perpendicular plastic wheel and squeegee. To enhance performance the tablets will:

1. Effervesce oxygen to degas the odors from solution.
2. The bubbles will entrain with the grease cap layer ensuring buoyancy.
3. Improve phase separation of FOG (fats, oils and greases) out of the water column.
4. Improve suspended solids settling by charge agglomeration with the Aqua Kleer protein and bubbling action.
5. Help prevent the recreation of the odors by keeping the system aerobic and binding hydrogen sulfide with the derivative of *Ricinus communis* seed extract.)

Tablet Ingredients 1. (30-50%) sodium carbonate peroxydrate—granular and coated, and stabilized.
2. (5-20%) AppTec Aqua Kleer® *Moringa oleifera* seed protein powder.
3. (0.5-20%) AppTec Dieoshield *Ricinus communis* seed extract paste which has been processed into a dry flowable powder using a proprietary fluidized-bed processing technique.
4. (2-3%) sodium C14-16 olefin sulfonate-surfacant-bioactive or a proprietary blend on non-ionic ethoxlated alcohols which have been dried and flaked.
5. (10-15%) binders and fillers—polyethylene glycol 6k, polyvinyl pyrrolidone (pvp) k-30, shellac natural gum, microcrystalline cellulose (mcc), lactose, hydroxypropyl methyl cellulose (hpmc), ethyl cellulose (ec), sodium chloride, talc.
6. (1.0%) sodium bi-carbonate=pH and alkalinity buffer and filler.
7. No bacteria in this formulation.

Wastewater Treatment Pucks

This product forms stable and structurally sound, wastewater pretreatment pucks (or tablets) using the listed ingredients in a 2.5" to 3.0" tablet diameter size with a weight of about 0.5 pounds. These tablets are produced specifically to be used to pre-treat wastewater streams before formal treatment process. To enhance performance the tablets will:

1. Effervesce oxygen to degas the odors from solution.
2. Keep the wastewater stream minimally aerobic.
3. Help prevent corrosive acid damage by neutralizing existing acids and preventing the formation of new acid at the laminar zones within piping structure.
4. The bubbles will entrain with the grease cap layer ensuring buoyancy and maintain aerobic conditions.
5. Improve phase separation of FOG (fats, oils, and greases) out of the water column.
6. Improve suspended solids settling by charge agglomeration with the Aqua Kleer® protein and bubbling action increasing suspended particle collisions thereby increasing settling rates.
7. Help prevent the recreation of the odors by keeping the system aerobic and binding hydrogen sulfide with the Deoshield®.
8. Inoculate each layer (grease cap, water column and settled sludge blanket layer) within the waste stream with the proper microbes.

Tablet Ingredients 1. (30-50%) sodium carbonate peroxydrate—granular and coated, time-released and stabilized.
2. (5-20%) AppTec Aqua Kleer® *Moringa oleifera* seed protein powder.
3. (0.5-20%) AppTec Dieoshield *Ricinus communis* seed extract paste which has been processed into a dry flowable powder using a proprietary fluidized-bed processing technique.
4. (2-3%) sodium C14-16 olefin sulfonate-surfacant-bioactive or a proprietary blend on non-ionic ethoxlated alcohols which have been dried and flaked.
5. (10-15%) binders and fillers binders and fillers—polyethylene glycol 6k, polyvinyl pyrrolidone (pvp) k-30, shellac natural gum, microcrystalline cellulose (mcc), lactose, hydroxypropyl methyl cellulose (hpmc), ethyl cellulose (ec), sodium chloride, talc.
6. (1.0%) sodium bi-carbonate—pH and alkalinity buffer and filler.
7. (2-5%) bacterial component. *Bacillus* (e.g. *Bacillus licheniformis, Bacillus subtilis, Bacillus polymyxa, Bacillus megaterium*) and *Pseudomonas* (eg. *Pseudomonas putida*) and various species and strains of fungi (e.g. *Hanerochaete chrysosporium* and *Aspergillus niger*).

D. Grease Trap Treatment Pucks

This product forms stable and structurally sound, wastewater pretreatment pucks (or tablets) using the listed ingredients in a 2.5" to 3.0" tablet diameter size with a weight of about 0.5 pounds. These tablets are produced specifically to be used to pre-treat wastewater streams before formal treatment process. To enhance performance the tablets will:
1. Effervesce oxygen to degas the odors from solution.
2. Keep the grease trap minimally aerobic.
3. Help prevent corrosive acid damage by neutralizing existing acids and preventing the formation of new acid at the laminar zones within piping structure.
4. The bubbles will entrain with the grease cap layer ensuring buoyancy and maintain aerobic conditions.
5. Improve phase separation of FOB (fats, oils and greases) out of the water column.
6. Improve suspended solids settling by charge agglomeration with the Aqua Kleer® protein and bubbling action increasing suspended particle collisions thereby increasing settling rates.
7. Help prevent the recreation of the odors by keeping the system aerobic and binding hydrogen sulfide with the derivative of *Ricinus communis* seed extract.)
8. Inoculate each layer (grease cap, water, column and settled sludge blanket layer) within the waste stream with the proper microbes.

Table Ingredients
1. (30-50%) sodium carbonate peroxydrate—granular and coated, time-released and stabilized.
2. (5-20%) AppTec Aqua Kleer® *Moringa oleifera* seed protein powder.
3. (0.5-20%) AppTec Dieoshield *Ricinus communis* seed extract paste which has been processed into a dry flowable powder using a proprietary fluidized-bed processing technique.
4. (2-3%) sodium C14-16 olefin sulfonate—surfactant—bioactive or equivalent.
5. (10-15%) binders and fillers binders and fillers—polyethylene glycol 6k, polyvinyl pyrrolidone (pvp) k-30, shellac natural gum, microcrystalline cellulose (mcc), lactose, hydroxypropyl methyl cellulose (hpmc), ethyl cellulose (ec), sodium chloride, talc.
6. (1.0%) sodium bi-carbonate—pH and alkalinity buffer and filler.
7. (2-5%) *Bacillus* (e.g. *Bacillus licheniformis, Bacillus subtilis, Bacillus polymyxa, Bacillus megaterium*) and *Pseudomonas* (eg. *Pseudomonas putida*) and various species and strains of fungi (e.g. *Hanerochaete chrysosporium* and *Aspergillus niger*)

E. Portable Toilet Pucks
This product forms stable and structurally sound, portable toilet treatment mini-pucks (or tablets) using the listed ingredients in a 0.75" to 1.5" tablet diameter size with a weight of about 40 grams to 50 grams. These tablets are produced specifically used to pre-treat waste in holding tanks before and during transport to traditional waste treatment facilities. They are designed to be environmentally friendly alternative to currently used products that contain toxic compounds such as methyl ammonia, quaternary ammonia, and formaldehyde. To enhance performance the tablets will:
1. Effervesce oxygen to degas the odors from solution.
2. Keep the waste container aerobic.
3. Help prevent corrosive acid damage by neutralizing existing acids and preventing the formation of new acid.
4. Pre-treat the waste by aiding the breakdown of solids.
5. Improve suspended solids settling by charge agglomeration with the Aqua Kleer® protein and bubbling action increasing suspended particle collisions thereby increasing settling rates.
6. Help prevent the recreation of the odors by keeping the system aerobic and binding hydrogen sulfide with the Deoshield®.
7. Inoculate each layer (grease cap, water, column and settled sludge blanket layer) within the waste stream with the proper microbes.
8. Provide a pleasant fragrance that is biodegradable and non-toxic.
9. Provide a non-toxic dark blue dye that is colorfast in urine acidic environments, while being non-staining
10. Tablets should be coated for ease of handling.
11. Tablets should be sealed in protective packaging to prevent loss of fragrance.

Table Ingredients
1. (20%) sodium carbonate peroxydrate—granular and sulfate coated, and stabilized.
2. (2%) calcium peroxide.
3. (2%) sodium C14-16 olefin sulfonate-surfacant-bioactive or a proprietary blend on non-ionic ethoxlated alcohols which have been dried and flaked.
4. (10%) sugar—(lactose, fructose or maltose monohydrate powder).
5. (used as filler) sodium chloride.
6. (used as filler) sodium carbonate.
7. (1.0%) sodium bi-carbonate.
8. (0.05%) sodium phosphate, monobasic.
9. (0.025%) sodium phosphate, dibasic.
10. (as needed) binders and fillers—polyethylene glycol 6k, polyvinyl pyrrolidone (pvp) k-30, shellac natural gum, microcrystalline cellulose (mcc), lactose, hydroxypropyl methyl cellulose (hpmc), ethyl cellulose (ec), sodium chloride, talc.
11. (1.0%) biodegradable dyes—non toxic—high strength blue yet nonstaining, stable in acid conditions
12. (0.5%) biodegradable—odor masking fragrance
13. (5.0-10%) AppTec Aqua Kleer® *Moringa oleifera* seed protein powder.
14. An AppTec Dieoshield *Ricinus communis* seed extract paste which has been processed into a dry flowable powder using a proprietary fluidized-bed processing technique.

E. Drain Treatment—Insect Control
Powdered product Ingredients (percent by weight)
1. (20%) sodium carbonate peroxydrate—granular and coated, time-released and stabilized.
2. (5%) Biodegradable organic botanical material such as dehydrated leaf or chaff ground into a fine powder or biodegradable microsponge material derived from the waste product of corn, soy, barley, rye or drumstick tree seed.
3. (5%) AppTec Aqua Kleer® *Moringa oleifera* seed protein powder.
4. (0.5%) Concentrated neem tree (*Azadirachta indica*) oil extract containing a high concentration of the active ingredient azadirachtin.
5. (5-10%) PG/PEG 6000
10. (as needed to make up difference) binders and fillers—polyethylene glycol 6k, polyvinyl pyrrolidone (pvp) k-30, shellac natural gum, microcrystalline cellulose (mcc), lactose, hydroxypropyl methyl cellulose (hpmc), ethyl cellulose (ec), sodium chloride, talc.
11. (0.5%) fragrance biodegradable—odor masking fragrance (may be omitted)

Additional Aspects of the Present Invention
Especially when treating large bodies of water, such as a pond or a wastewater container, an efficient method of dispersing the inventive pucks would be desirable. Thus, as another aspect of the present invention, there is envisioned a hopper for containing a plurality of pucks. The hopper can be humidity controlled to prevent pucks from prematurely reacting to moisture. The hopper can be attached to, for example, a boat, for example at the side or stem of a boat. The hopper includes, preferably, a motor with a battery or other power supply, such as solar power, an auger and a retaining door. Using this device, a boat can traverse a body of water to be treated and the hopper will release pucks into the water at a desired rate. When treating a water or wastewater moving through a treatment system (sewer pipes, lift stations, treatment basins etc.) it is possible to place a hopper at a fixed location will automatically deliver tablets to the wastestream at a desired rate.

Another device of the present invention automatically tosses or ejects pucks into a body of surface water, such as a pond, lake or lagoon. The device comprises a hopper to store a quantity of pucks, and the hopper can be humidity controlled to prevent the pucks from reacting prematurely with moisture. The hopper would then deliver the pucks to a launcher mechanism, such as a spring loaded launcher mechanism. The launcher mechanism would then eject the pucks, preferably at different velocities and in different directions, to allow for maximum distribution. The device can be electronically controlled and programmable. The power source can be any conventional source, such as a battery, solar power or external power source.

Also for treating a body of water, such as a pond or waste water container, and depending on the conditions being treated, the buoyancy of the components within the puck can be important. As the tablet disintegrates and releases its components, controlling where particular ingredients such as the buffers and the biological (microbial) portions end up can greatly increase the likelihood of successful treatment. For example, a grease cap layer on the water can be treated with a puck having those mentioned components with positive buoyancy. Suspended solids in a water column can be treated with components having neutral buoyancy. A sediment layer can be treated with components having negative buoyancy. The advantage to using this method is to add only one puck containing components of various buoyancies, thereby treating the surface middle and bottom with the correct components simultaneously.

Positive buoyancy components include bran flakes, saw dust and barley straw. Substrates for neutrally buoyant puck include dissolving substrates, sodium bicarbonate, sodium carbonate, micro-sponge and polymers. For negatively buoyant components one can use dense or heavy clays and Diatomaceous Earth and zeolites which will sink. These components can act as substrate or carrier onto which the microbes can be lyophilized or adsorbed. The type of organism applied to the substrate will depend upon the type and location of the contaminant which is to be broken down by the microbe. If the contaminant is floating surface oil and grease than a positively buoyant substrate can be chosen and microbial strains applied to it that are useful in breaking down oil an grease used depends upon the organism chosen to be applied to the substrate, where the organism is chosen for its ability to break down specific contaminants located in that area. The amount used can be part of the percent by weight listed in the bacterial portion of the above products.

In addition to the components mentioned above, it may be desirable to hold the pucks themselves at a desired depth in the water as they disintegrate. This may be necessary to insure the maximum dispersion within the water system. One way to do this is to provide for a tube with a cage at its bottom, wherein the cage is made of a non-corrosive metal or plastic. The tube is lowered to the desired depth and then the puck or pucks are added. Preferably, the puck or pucks will have sufficient negative buoyancy so that they will sink down to the cage. The pucks can be stored in a hopper of the type described above, which can be attached to the tube. Pucks are then released from the hopper into the tube.

Discussed above are preparations for treating gray grease, sometimes called brown grease. A further aspect of this invention is to convert the gray grease to yellow grease, which can be used as a feed stock in the production of, for example, biodiesel fuel.

The problems with processing of gray grease into a useful feed-stock for biodiesel production are that it is emulsified with water, it contains embedded particles and there are mixtures of different compounds contaminating the grease.

To overcome these problems, the gray grease is first dewatered by a combination of heating and vibration, such as ultrasound. It is then exposed to various wavelengths of light (within the ultraviolet range) Thereafter, pucks or granules of the type disclosed above for treating a grease cap is used to inoculate the grease cap layer. This can occur in a holding tank which contained the gray grease.

Thereafter, the water can be decanted from the bottom of the tank, preferably with a vortexing pump (separates oil and water), with the oil portion being sent back into the tank. Once decanted, the waste oil or grease can be vibrated and heated to aid in the phase separation with different portions being removed from different levels of the holding tank.

EXAMPLES

The present Examples relate to three products: the 150 gm wastewater puck; the 50 gram wastewater puck; and the 150 gram pond clarifier puck.

1. The 150 gram ADS AquaPucks™ Wastewater Treatment Puck is made using the standard tableting practice of batch production. The ingredients listed below are mixed together with a total weight of 2000 lbs per batch. Colton 16 station rotary press with a 3.0" tablet punches and 12" max depth of fill and 40 Klbs above and below yielding a compression of 40 tons using the standard method outlined in the APA Tableting Specification Manual. The press is set at ¾ maximum pressures and speed was adjusted to ¼ of full to prevent capping. The formulation used is listed below:

| ADS AQUAPUCKS WASTE WATER TREATMENT COMPONENTS PER PUCK | | |
|---|---|---|
| PUCK SIZE (3.0" DIA) | % by wt. | Grams |
| *Moringa* Seed Powder | 5 | 7.5 |
| NA-PERCARBONATE | 20 | 30 |
| NA-CARBONATE | 5 | 7.5 |
| NA-BICARBONATE | 1 | 1.5 |
| BACTERIA on substrates | 5.1 | 8.0 |
| POLYETHYLENE GLYCOL, PG/PEG 6000 | 6.0 | 9.0 |
| NA-OLE SULFO C14-16 (Surfactant) | 2.5 | 3.75 |
| BINDERS (PVP, SHELLAC) | | |
| POLYVINYL PYRROLIDONE, PVP K-30 | 0.2 | .3 |
| SHELLAC (Natural Gum) | 0.1 | .15 |
| FILLERS (MCC, SDL) | | |
| Microcrystalline Cellulose (MCC) | 2.5 | 3.75 |
| Spray Dried Lactose (SDL) | 20.0 | 30 |
| NaCl | 31.4 | 47.1150 |
| TOTAL | 100% | GMS |

The bacterial portion consists of the following types: *Bacillus licheniformis, Bacillus subtilis, Bacillus polymyxa,*

*Bacillus megaterium, Pseudomonas putida*, and *Lactobacillus* sp.). For this preparation, the bacteria were lyophilized onto three substrates (powdered bran flake, Calcium Carbonate, and clay powder).

The ingredients were placed in a large stainless steal tumbling mixer and tumbled for 3 minutes to insure homogeneity of the mixture. The mixture was then gravity feed into the rotary press for tableting.

The depth of fill was adjusted to create pucks of approximately 150 grams of mass.

Tableting was performed in a temperature and humidity controlled room to improve performance.

After tableting produced pucks were then shrink-wrapped into sleeves of three with an acetate film and then placed in air tight plastic buckets containing 30 sleeves, for storage.

Testing and evaluation was performed in a real-world wastewater treatment facility. The tests conducted evaluated the ability of the pucks in removing odors and preventing odorous compound reformation in a wastewater effluent from a manufacturing plant. The sulfides analyzed included hydrogen sulfide, carbonyl sulfide, methyl mercaptan, dimethyl sulfide, and carbon disulfide. These compounds made up the majority responsible for odors at this field trail. The plant has a wastewater pretreatment facility capable of treating 2 million gallons of wastewater per day. The pucks were added to the lift station pumping the wastewater to a pair of 400,000 gallon equalization tanks. The treated effluent is than discharged into a sanitary sewer leading to the town's municipal wastewater treatment facility for further treatment. After a 6 week trail, it was determined that 1.52 lbs of the pucks are capable of removing 1.0 pounds of sulfur from the wastewater. This resulted in a 92% reduction, to acceptable levels, from the predicted average daily sulfide level using 3.0 pounds of pucks in 1.7 million gallons of wastewater. It was also determined that dosages required to maintain sulfide removal rates varied with temperature, COD (chemical oxygen demand) levels and wastewater detention times (HRT).

The dosage/response chart based on 0.7 million gallons of wastewater per day, below can be used as a guideline for calculating the correct amount of material to neutralize sulfide compounds to acceptable levels assuming initial concentrations of 1390 mg/l or parts per million.

| Water T (deg. C.) | COD (mg/L) | | | | |
|---|---|---|---|---|---|
| | 100 | 200 | 300 | 400 | 500 |
| | Predicted Aqua-Puck dosing requirement (lb/d) | | | | |
| High HRT = 26.3 hr | | | | | |
| 20 | 2.8 | 3.0 | 3.2 | 3.4 | 3.5 |
| 25 | 4.1 | 4.4 | 4.6 | 4.8 | 5.1 |
| 30 | 5.9 | 6.2 | 6.6 | 6.9 | 7.3 |
| Average HRT = 18.8 hr | | | | | |
| 20 | 1.7 | 1.8 | 2.0 | 2.2 | 2.4 |
| 25 | 2.5 | 2.7 | 2.9 | 3.2 | 3.4 |
| 30 | 3.6 | 3.9 | 4.3 | 4.6 | 5.0 |
| Low HRT = 14.6 hr | | | | | |
| 20 | 1.0 | 1.2 | 1.4 | 1.5 | 1.7 |
| 25 | 1.5 | 1.8 | 2.0 | 2.3 | 2.5 |
| 30 | 2.3 | 2.6 | 3.0 | 3.3 | 3.7 |

Figure 2:
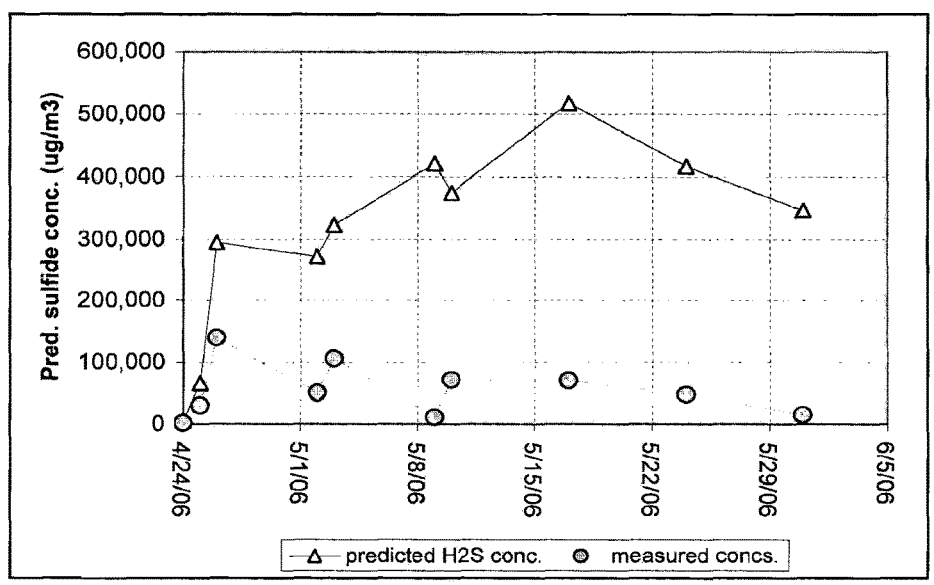
FIG. 2 is a comparison of measured TA-220 liquid-phase sulfide concentration during Aqua-Puck Dosing period to predicted liquid-phase sulfide concentration using simple correlation equation based on HRT and COD concentration.

FIG. 1 shows a comparison of measured liquid-phase sulfide production during Aqua-Puck Dosing period to predicted liquid-phase sulfide production using simple correlation equation based on TA-HRT and COD concentration FIG. 2 shows a comparison of measured TA-220 liquid-phase sulfide concentration during Aqua-Puck Dosing period to predicted liquid-phase sulfide concentration using simple correlation equation based on HRT and COD concentration 2. The 50 gram ADS AquaPucks™ Wastewater Treatment Mini-Puck is made using the standard tableting practice of batch production. The ingredients listed below are mixed together with a total weight of 2000 lbs per batch. Colton 16 station rotary press with a 2.0" tablet punches and 12" max depth of fill and 40 Klbs above and below yielding a compression of 40 tons using the standard method outlined in the APA Tableting Specification Manual. The press is set at ¼ maximum pressures and speed was adjusted to ¼ of full to prevent capping.

The same method as in the manufacture of the 150 gm pucks was used to make the fifty gram tablets with the exception that 2" diameter punches were used and the depth of fill was adjusted to create pucks of the correct mass.

The formulation used is listed below:

| ADS AQUAPUCKS WASTE WATER TREATMENT COMPONENTS PER PUCK | | |
|---|---|---|
| PUCK SIZE (2.0" DIA) | % by wt. | Grams |
| *Moringa* Seed Powder | 5 | 2.5 |
| NA-PERCARBONATE | 20 | 10 |
| NA-CARBONATE | 5 | 2.5 |
| NA-BICARBONATE | 1 | 0.5 |
| BACTERIA on substrates | 5.1 | 2.55 |
| POLYETHYLENE GLYCOL, PG/PEG 6000 | 6.0 | 3.0 |
| NA-OLE SULFO C14-16 (Surfactant) | 2.5 | 1.25 |
| BINDERS (PVP, SHELLAC) | | |
| POLYVINYL PYRROLIDONE, PVP K-30 | 0.2 | 0.1 |
| SHELLAC (Natural Gum) | 0.1 | 0.05 |
| FILLERS (MCC, SDL) | | |
| Microcrystalline Cellulose (MCC) | 2.5 | 1.25 |
| Spray Dried Lactose (DSL) | 20.0 | 10 |
| NaCl | 31.4 | 15.5250 |
| TOTAL | 100% | GMS |

The bacterial portion consists of the following types *Bacillus licheniformis—Bacillus subtilis, Bacillus polymyxa, Bacillus megateriurn, Pseudomonas putida*, and *Lactobacillus* sp.). For this preparation, the bacteria were lyophilized onto three substrates (powdered bran flake, Calcium Carbonate, and clay powder).

A field trial was conducted at a country club having a series of three 500 gallon traps leaving their restaurant and entering a sanitary sewer. Each of the traps was pumped out completely every three weeks as mandated by the municipality. Before trials with the pucks and even though this was being conducted, the effluent leaving the traps was routinely exceeding the clubs discharge permit guidelines for BOD, COD, TSS and O&G. This had resulted in expensive fines and surcharges. There was also a tremendous amount of odor emanating form the traps which was offensive to the club members. Field testing of the 50 gram pucks in an external grease interceptor has resulted positively in the following data.

| Date | Bod | Tss | Cld | Ph |
|---|---|---|---|---|
| May 4, 2006 | 9590 | 1800 | 919 | 7.56 |
| Jun. 6, 2006 | 23.7 | 84 | 37.3 | 7.56 |

-continued

| Date | Bod | Tss | Cld | Ph |
|---|---|---|---|---|
| Jun. 15, 2006 | 152 | 830 | 44.3 | 7.56 |
| Jun. 20, 2006 | 162 | 668 | 51.2 | 7.45 |
| Jun. 29, 2006 | 136 | 908 | 12.2 | 7.21 |
| Oil and Grease | | | | |
| May 10, 2006 | 242 mg/l | | | |
| Jun. 6, 2006 | 120 mg/l | | | |
| Jun. 15, 2006 | 43.9 mg/l | | | |
| Jun. 20, 2006 | 150 mg/l | | | |
| Jun. 29, 2006 | 108 mg/l | | | |

The data shows a tremendous increase in efficiency of the trap resulting in a 98.6% reduction in BOD (Biological oxygen demand) 49.6% reduction in TSS (Total suspended Solids) 98.6% reduction in COD (Chemical Oxygen Demand) and a 55.4% reduction in Oil and Grease. In addition the odors emanating from the traps were eliminated. These reductions in wastewater leaving the trap were achieved by applying 3 lbs per trap three times per week. The reductions brought the club back into compliance with their discharge permit and eliminated their fines and surcharges.

3. The 150 gram ADS AquaPucks™ Pond Clarifier Puck is made using the standard tableting practice of batch production. The ingredients listed below are mixed together with a total weight of 2000 lbs per batch. Colton 16 station rotary press with a 3.0" tablet punches and 12" max depth of fill and 40 Klbs above and below yielding a compression of 40 tons using the standard method outlined in the APA Tableting Specification Manual. The press is set at ¾ maximum pressures and speed was adjusted to ¼ of full to prevent capping. The formulation used is listed below:

| ADS AQUAPUCKS WASTE WATER TREATMENT COMPONENTS PER PUCK | | |
|---|---|---|
| PUCK SIZE (3.0" DIA) | % by wt. | Grams |
| Dehydrated and powdered Barley chaff | 25 | 37.5 |
| *Moringa* Seed Powder | 10 | 15 |
| NA-PERCARBONATE | 20 | 30 |
| BACTERIA on substrates | 5.1 | 8.0 |
| POLYETHYLENE GLYCOL, PG/PEG 6000 | 6.0 | 9.0 |
| BINDERS (PVP, SHELLAC) | | |
| POLYVINYL PYRROLIDONE, PVP K-30 | 0.2 | .3 |
| SHELLAC (Natural Gum) | 0.1 | .15 |

| ADS AQUAPUCKS WASTE WATER TREATMENT COMPONENTS PER PUCK | | |
|---|---|---|
| PUCK SIZE (3.0" DIA) | % by wt. | Grams |
| FILLERS (MCC, SDL) | | |
| Microcrystalline Cellulose (MCC) | 2.5 | 3.75 |
| Spray Dried Lactose (SDL) | 15.0 | 22.5 |
| NaCl | 22.1 | 33.15150 |
| TOTAL | 100% | GMS |

The bacterial portion consists of the following types *Bacillus licheniformis—Bacillus subtilis, Bacillus polymyxa, Bacillus megaterium, Pseudomonas putida*, and *Lactobacillus* sp.). For this preparation, the bacteria were lyophilized onto three substrates (powdered bran flake, Calcium Carbonate, and clay powder).

The same method as in the manufacture to make 150 gm wastewater pucks was used to make the 150 gram pond clarifier pucks with the exception that 3" diameter punches were used and the depth of fill was adjusted to create pucks of the correct mass.

What is claimed:

1. A water treatment puck comprising:
    a. an oxidative alkali in a concentration from 30 to 50 percent by weight of the puck;
    b. a clarifying agent comprising a dry powdered form of an activated botanical protein obtained from drumstick tree seed material (genus *Moringa*) in a concentration from 5 to 20 percent by weight of the puck; and
    c. a dry powdered form of a *Ricinus* seed extract in a concentration from 0.5 to 20 percent by weight of the puck,
    wherein the puck is a compressed homogenous mixture.

2. The water treating puck of claim 1, further comprising one or more microorganisms.

3. The water treating puck of claim 2, wherein the microorganism is one or a combination of *Bacillus, Pseudomonas* and *Lactobacillus*.

4. The water treating puck of claim 1, wherein the oxidative alkali is sodium carbonate peroxyhydrate, sodium perborate or sodium peroxide.

5. The water treating puck of claim 1, further comprising a positive buoyancy component, a neutrally buoyant component, a negatively buoyant component or a combination thereof.

\* \* \* \* \*